US007682762B2

(12) United States Patent
Levy et al.

(10) Patent No.: US 7,682,762 B2
(45) Date of Patent: Mar. 23, 2010

(54) PROCESS FOR PREPARING ORGANIC PHOTOSENSITIVE PIGMENT

(75) Inventors: Daniel V. Levy, Rochester, NY (US); Liang-bih Lin, Rochester, NY (US); Jin Wu, Webster, NY (US)

(73) Assignee: Xerox Corporation, Norwalk, CT (US)

( * ) Notice: Subject to any disclaimer, the term of this patent is extended or adjusted under 35 U.S.C. 154(b) by 388 days.

(21) Appl. No.: 11/800,822

(22) Filed: May 8, 2007

(65) Prior Publication Data

US 2008/0280223 A1 Nov. 13, 2008

(51) Int. Cl.
*G03G 5/06* (2006.01)
*C07D 487/22* (2006.01)

(52) U.S. Cl. ...................... 430/59.4; 430/59.5; 540/141

(58) Field of Classification Search ................ 430/59.4, 430/116, 137.22, 59.5; 540/141
See application file for complete search history.

(56) References Cited

U.S. PATENT DOCUMENTS

| | | | | |
|---|---|---|---|---|
| 5,164,493 | A | 11/1992 | Mayo et al. | |
| 2005/0145140 | A1 * | 7/2005 | Babler | 106/493 |
| 2006/0286468 | A1 * | 12/2006 | Chambers et al. | 430/58.8 |
| 2007/0098802 | A1 * | 5/2007 | Farr et al. | 424/489 |

OTHER PUBLICATIONS

STIC search of Jul. 6, 2009.*
Wang et al. Nature vol. 437 Sep. 2005 pp. 121-124.*

* cited by examiner

*Primary Examiner*—John L Goodrow
(74) *Attorney, Agent, or Firm*—Pillsbury Winthrop Shaw Pittman LLP

(57) ABSTRACT

Processes for making photosensitive organic pigments for use in imaging members, specifically processes for making photosensitive phthalocyanine pigments having a specific nanocrystal form. Embodiments include a copper phthalocyanine nanocrystal with good charge generation for use in the formulation of a charge generating layer and narrow particle size distribution.

20 Claims, 3 Drawing Sheets

FIG. 2A
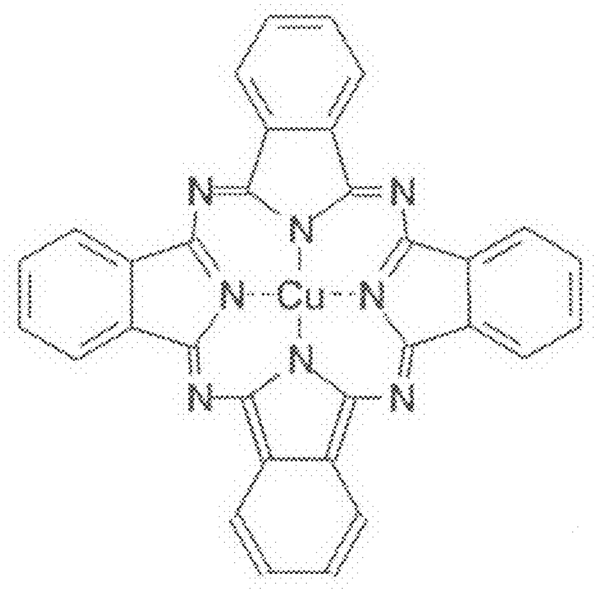
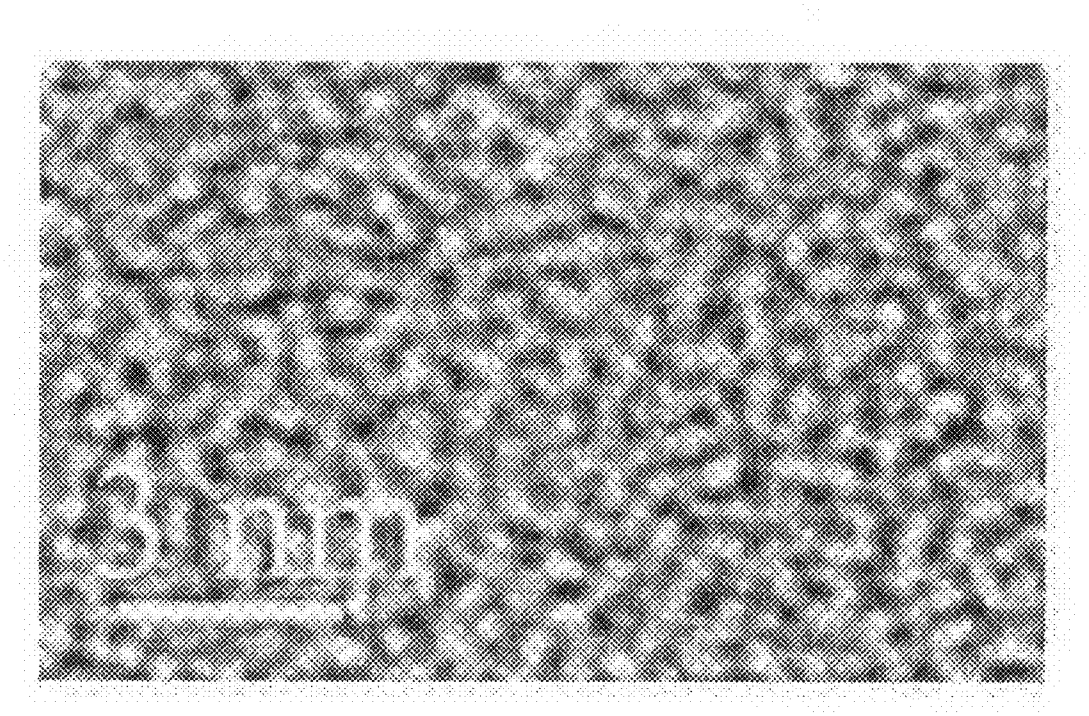
FIG. 2B

PROCESS FOR PREPARING ORGANIC PHOTOSENSITIVE PIGMENT

TECHNICAL FIELD

The present disclosure relates generally to organic photosensitive pigments used in imaging members, such as layered photoreceptor devices, and novel processes for producing the pigments. The imaging members can be used in electrophotographic, electrostatographic, xerographic and like devices, including printers, copiers, scanners, facsimiles, and including digital, image-on-image, and like devices. More specifically, the present embodiments relate to processes for preparing an organic photosensitive pigment having a nanocrystal form with high photosensitivity and narrow particle size distribution.

BACKGROUND

Electrophotographic imaging members, e.g., photoreceptors, typically include a photoconductive layer formed on an electrically conductive substrate. The photoconductive layer is an insulator in the substantial absence of light so that electric charges are retained on its surface. Upon exposure to light, charge is generated by the photoactive or photosensitive pigment, and under applied field charge moves through the photoreceptor and the charge is dissipated.

In electrophotography, also known as xerography, electrophotographic imaging or electrostatographic imaging, the surface of an electrophotographic plate, drum, belt or the like (imaging member or photoreceptor) containing a photoconductive insulating layer on a conductive layer is first uniformly electrostatically charged. The imaging member is then exposed to a pattern of activating electromagnetic radiation, such as light. Charge generated by the photoactive pigment move under the force of the applied field. The movement of the charge through the photoreceptor selectively dissipates the charge on the illuminated areas of the photoconductive insulating layer while leaving behind an electrostatic latent image. This electrostatic latent image may then be developed to form a visible image by depositing oppositely charged particles on the surface of the photoconductive insulating layer. The resulting visible image may then be transferred from the imaging member directly or indirectly (such as by a transfer or other member) to a print substrate, such as transparency or paper. The imaging process may be repeated many times with reusable imaging members.

An electrophotographic imaging member may be provided in a number of forms. For example, the imaging member may be a homogeneous layer of a single material such as vitreous selenium or it may be a composite single layer containing charge photogenerating and charge transporting compounds and other materials. In addition, the imaging member may be layered. These layers can be in any order, and sometimes can be combined in a single or mixed layer.

Typical multilayered photoreceptors have at least two layers, and may include a substrate, a conductive layer, an optional charge blocking layer, an optional adhesive layer, a photogenerating layer (sometimes referred to as, and used herein interchangeably, a "charge generation layer," "charge generating layer," or "charge generator layer"), a charge transport layer, an optional overcoating layer and, in some belt embodiments, an anticurl backing layer. In the multilayer configuration, the active layers of the photoreceptor are the charge generating layer (CGL) and the charge transport layer (CTL).

As more advanced, higher speed electrophotographic copiers, duplicators and printers were developed, however, degradation of image quality was encountered during extended cycling. The complex, highly sophisticated duplicating and printing systems operating at very high speeds have placed stringent requirements, including narrow operating limits, on the imaging members. Thus, photoreceptor materials are required to exhibit, efficient charge generation and charge transport properties, and structural integrity and robustness so as to withstand mechanical abrasion during image development cycles.

Organic photosensitive pigments are widely used as photoactive components in charge generating layers. One such pigment used in the charge generating layer in electrophotographic devices is phthalocyanine (Pc). Phthalocyanines represent one of the key components of photoreceptors because of their high efficiency of charge generation. As explained, for example, in U.S. Pat. No. 5,164,493, which is hereby incorporated by reference in its entirety, polymorphism or the ability to form distinct solid state forms is well known in phthalocyanines and will affect its photoactive properties. For example, there are several titanyl phthalocyanine (TiOPc) crystal forms, or polymorphs, known to be useful in photoreceptor devices. The control of the crystal form of phthalocyanines, such as TiOPc, is critical for obtaining the desired photoactive properties, such as high photosensitivity.

Standard preparation of phthalocyanines involves synthesis at high temperature, isolation and purification, dissolution in acid followed by subsequent precipitation, and conversion to different crystal structures using organic solvents. The resulting product is expectedly in large aggregates which must be subsequently milled down to form a dispersion. The overall process results in a wide distribution of particle sizes (e.g., generally from about 100 to about 600 nm, depending on the binder and solvent system used). These wide distributions are of concern because it has been observed that the presence of large particles can cause problems such as increased charge-deficient spots (CDS) and print uniformity.

As such, processes for obtaining phthalocyanines for electrophotographic application are generally complex, multi-step processes and therefore the ability of obtaining a consistent final product with all the desired properties, including size distribution, may not be very reproducible.

The term "nanocrystal" is herein generally used interchangeably with the term "nanoparticle."

BRIEF SUMMARY

According to embodiments illustrated herein, there is provided improved processes for making a photosensitive pigment for use in electrophotographic applications that address the shortcomings discussed above.

In one embodiment, there is provided a process for preparing an organic photosensitive pigment having a nanocrystal form, comprising (a) combining together a liquid phase, a solid phase, and a solution to form a liquid-solid-solution, wherein the liquid phase comprises a fatty acid and an alcohol solvent, the solid phase comprises a sodium salt of the fatty acid, and the solution comprises metal salts, (b) mixing the liquid-solid-solution to induce a phase transfer reaction, (c) heating the reaction to generate phthalocyanine complexes with metal ions from the solid phase to form nanocrystals of the metal phthalocyanine, (d) preparing the metal phthalocyanine nanocrystals for use as an organic photosensitive pigment.

In other embodiments, the metal phthalocyanine nanocrystals are further converted to a second nanocrystal form for use as the organic photosensitive pigment, the conversion comprising (e) mixing the metal phthalocyanine nanocrystals in a second solvent, (f) filtering the converted phthalocyanine nanocrystals in a vacuum funnel, (g) washing the converted phthalocyanine nanocrystals, and (h) drying the converted phthalocyanine nanocrystals in a vacuum oven.

In another embodiment, there is provided an organic photosensitive pigment having a nanocrystal form made from the above-described process.

A further embodiment provides an imaging member comprising a substrate, a charge generating layer disposed on the substrate, at least one charge transport layer disposed on the charge generating layer, and an anticurl back coating disposed on the substrate on a side opposite to the charge transport layer, the charge generating layer comprising an organic photosensitive pigment having a nanocrystal form made from the above-described process.

Yet another embodiment provides a process for preparing an organic photosensitive pigment having a nanocrystal form, comprising (a) combining together a liquid phase, a solid phase, and a solution to form a liquid-solid-solution, wherein the liquid phase comprises a fatty acid and an alcohol solvent, the solid phase comprises a sodium salt of the fatty acid, and the solution comprises metal salts, (b) mixing the liquid-solid-solution to induce a phase transfer reaction between the solid phase and the solution phase, the reaction forming metal salts of the fatty acid in the solid phase, (c) heating the reaction to generate phthalocyanine complexes with metal ions from the solid phase to form nanocrystals of the metal phthalocyanine, (d) collecting the metal phthalocyanine nanocrystals that separate out from the solution phase, and (e) preparing the metal phthalocyanine nanocrystals for use as an organic photosensitive pigment.

BRIEF DESCRIPTION OF THE DRAWINGS

For a better understanding of the present embodiments, reference may be had to the accompanying figures.

FIG. 2A is an illustration of the chemical structure of copper phthalocyanine;

FIG. 2B is a transmission electron micrograph (TEM) of copper phthalocyanine nanocrystals obtained from the present embodiments.

DETAILED DESCRIPTION

Figure 1:
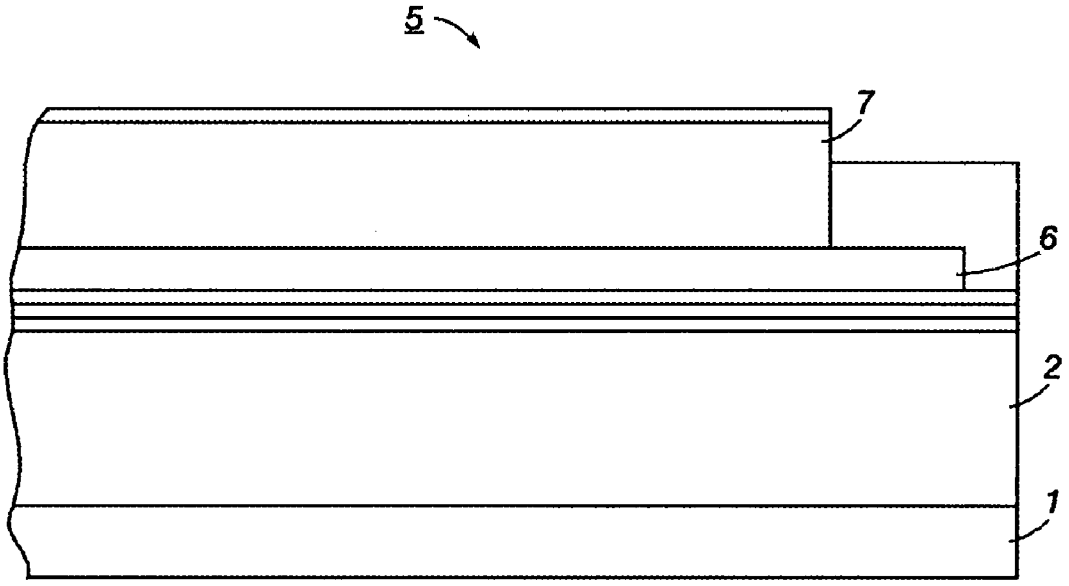
FIG. 1 is a cross-sectional view of an imaging member made according to the present embodiments.

It is understood that other embodiments may be utilized and structural and operational changes may be made without departure from the scope of the embodiments disclosed herein.

The embodiments relate to processes for making an organic photosensitive pigment, namely, a pigment comprising phthalocyanine (Pc), with good charge generation for use in the formulation of a charge generating layer. Moreover, the embodiments are directed generally to processes that consistently produce phthalocyanine nanocrystals, and provide better control in obtaining the desired phthalocyanine properties, such as for example, high photosensitivity, consistent particle size, narrow particle size distribution, and the like.

Commonly used processes for making organic photosensitive pigments result in wide particle size distributions which lead to increased charge-deficient spots (CDS) and print uniformity. To prevent CDS or other imaging problems, the processes are generally complex, and require multiple steps. A preparation that utilizes nanotechnology is able to circumvent these problems by generating crystals on the order of tens of nanometers (or less) with narrow particle size distributions.

As described in an article which is hereby incorporated by reference, there is a process using a solvent/water-based system by which to prepare phthalocyanine nanocrystals with a narrow particle size distribution. See Wang et al., A general strategy for nanocrystal synthesis. *Nature* 437, 121-24 (2005). The process allows for the generation of monodisperse phthalocyanine nanocrystals from a ternary system. The resulting crystals have narrow diameter size distribution. Transmission electron microscope (TEM) images of samples show that the nanocrystals are obtained in large quantities and with good uniformity.

The technique involves the formation of phthalocyanine through a phase-transfer process. In the ternary system, also described as liquid-solid-solution (LSS) system, the formation of the nanocrystals occurs on the interface between the LSS layers and relies on phase transfer to proceed. For the general nanocrystal preparation, the liquid phase comprises a fatty acid, an alcohol solvent, and a reactive species (if needed). In forming nanocrystals of an element or an oxide, additional reactive species are not needed. For all other species, including sulfides, selenides, fluorides, phthalocyanines, an anionic species is needed to form the desired nanocrystal. In the present embodiments, dicyanobenzene may be used as the reactive species which reacts to form the anionic phthalocyanine. The solid phase is comprised of a sodium salt of the fatty acid, while the solution phase contains the reactive metal species (typically coordinated to a chloride or acetate) in the alcohol and water. Upon mixing, a phase transfer of the metal ions occurs between the solid and solution phase, resulting in formation of reactive metal salts of the fatty acid in the solid phase (1). The reaction is then heated, for example in a sealed tube, and the metal species undergoes reaction with either the reactive species or, in the case of oxides, a reduction with the alcohol (2). The corresponding anion of the fatty acid complexes to the formed nanocrystal and when a critical mass is reached, the weight of the metal nanocrystals and the incompatibility between the hydrophobic surfaces of the nanocrystals (from the fatty acid alkyl chain) and their hydrophilic surroundings will cause the crystal and its hydrophobic fatty acid shell drop out of solution (3).

(1)

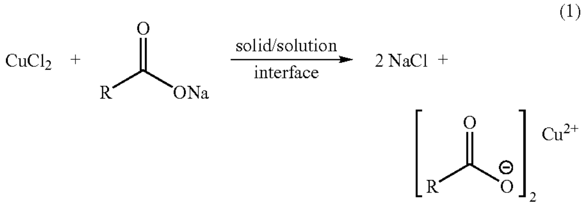

(2)

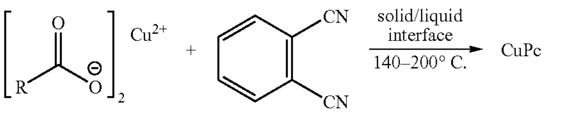

-continued (3)

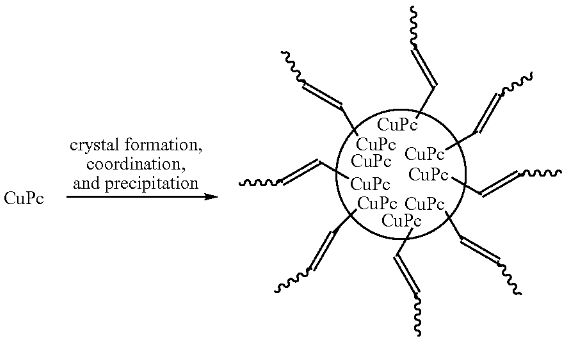

The nanocrystal product is isolated due to coordination of the corresponding anion of a fatty acid (e.g., a carboxylic acid when linoleic acid is used as the fatty acid) to the metal centers on the outside of the nanocrystal, which makes the surface of hydrophobic and thus insoluble. As a result, the nanocrystal precipitates from the hydrophilic system. The resulting crystals can then be easily collected from the bottom of the container. After collection, the crystals are recovered in the form of solid powders and observed to have consistent and narrow particle size distributions. The preparation of phthalocyanine nanocrystals with diameters of less than 1 nm represents a potential solution to the wide particle size distribution and larger particles observed with the current methodology.

Various combinations of components may be used to create the LSS phases. For example, in embodiments, the fatty acid may be selected from the following: unsaturated fatty acids such as butyric, caprioic, caprylic, capric, lauric, myristic, palmitic, stearic, arachidic, and behenic acids, saturated fatty acids such as myristoleic, palmitoleic, oleic, linoleic, alpha-linoleinic, arachidonic, eicosapentaenoic, erucic, and docosahexaenoic acids, and mixtures thereof. The alcohol solvent may be selected from any number of solvents having the formula $C_nH_{2n+2}O_x$, wherein n varies from 1 to 30 and x varies from 1 to 2, and includes branched structures. A few specific examples include ethanol, glycol, n-octanol, and mixtures thereof. In further embodiments, if the liquid phase includes a reactive species, such as for example, to form nanocrystals of phthalocyanine, the reactive species may be selected from the following: 1,2-dicyanobenzene and diiminoisoindoline, and mixtures thereof. The sodium salt of the fatty acid may be any salts of the corresponding fatty acids listed above, and mixtures thereof. The metal salt may be selected from the following: metal acetates, halides, bromates, chlorates, perchlorates, nitrates, nitrites, sulfonates, sulfites, phosphates, carbonates, benzoates, and mixtures thereof.

In specific embodiments, there is provided a process for preparing an organic photosenstive pigment having a nanocrystal form using the LSS ternary system described above. The process comprises combining together a liquid phase, a solid phase, and a solution to form a liquid-solid-solution, where the liquid phase comprises a fatty acid and an alcohol solvent, the solid phase comprises a sodium salt of the fatty acid, and the solution comprises metal salts. The liquid-solid-solution is then mixed or agitated to induce a phase transfer reaction between the solid phase and the solution phase in which the phase transfer of metal ions occurs spontaneously across the interface of the solid phase and the solution phase based on ion exchange, which leads to the formation of reactive metal salts of the fatty acid (1). As described above, the reaction is then heated, for example, in a sealed tube, and the metal species undergoes reaction with either the reactive species or a reduction with the alcohol (2). In embodiments, the reaction is heated from about 90° C. to about 200° C., or from about 140° C. to about 200° C. A spontaneous phase-separation occurs due to the weight of the metal nanocrystals and the incompatibility between the hydrophobic surfaces of the nanocrystals and their hydrophilic surroundings will cause the crystal to precipitate out of solution and be easily collected at the bottom of the container (3). The nanocrystals can also be re-precipitated from a solution and separated by adding an appropriate amount of ethanol to the bulky nanocrystal solutions or by force due to an external field.

After collection, the crystals are recovered in the form of solid powders. Then, the nanocrystals are prepared for use as an organic photosensitive pigment. The pigment can be used in the crystal structure formed in the reaction, or can undergo conversion to a different crystal form through mixing, by either stirring or rolling, either in the presence of glass beads or without, in a solvent. Examples of solvents include halogen-containing solvents, such as chloroform, chlorobenzene and dichlorobenzene; ketone solvents, such as cyclohexanone, methyl ethyl ketone and acetone; nitrile solvents, such as acetonitrile and benzonitrile; ester solvents, such as ethyl acetate and butyl acetate; alcohol solvents, such as methanol, ethanol, propanol, ethylene glycol and polyethylene glycol, and ether solvents, such as tetrahydrofuran, 1,4-dioxane, propyl ether, and butyl ether in an amide solvent, such as N,N-dimethylformamide, or N-methylpyrrolidone and other suitable solvents like pentane, hexane, cyclohexane benzene, toluene, xylene and the like. After conversion, the pigment can be collected by filtration through a fritted vacuum funnel and then washed with a suitable solvent like acetone, followed by drying in a vacuum oven for about 18 to about 20 hours, or overnight. Pigments can then be formulated into charge generating layers through dispersion in binders and a coating solvent. Examples of binders include polycarbonates, polyarylates, acrylate polymers, vinyl polymers, cellulose polymers, polyesters, polysiloxanes, polyamides, polyurethanes, poly(cyclo olefins), epoxies, and random or alternating copolymers thereof; and more specifically, polycarbonates such as poly(4,4'-isopropylidene-diphenylene)carbonate (also referred to as bisphenol-A-polycarbonate), poly(4,4'-cyclohexylidinediphenylene)carbonate (also referred to as bisphenol-Z-polycarbonate), poly(4,4'-isopropylidene-3,3'-dimethyl-diphenyl)carbonate (also referred to as bisphenol-C-polycarbonate), and the like. In embodiments, electrically inactive binders are comprised of polycarbonate resins with a molecular weight of from about 20,000 to about 100,000, or with a molecular weight $M_w$ of from about 50,000 to about 100,000 preferred. Examples of coating solvents used include ketones, alcohols, aromatic hydrocarbons, halogenated aliphatic hydrocarbons, ethers, amines, amides, esters, and the like. Specific solvent examples are cyclohexanone, acetone, methyl ethyl ketone, methanol, ethanol, butanol, amyl alcohol, toluene, xylene, chlorobenzene, carbon tetrachloride, chloroform, methylene chloride, trichloroethylene, tetrahydrofuran, dioxane, diethyl ether, dimethyl formamide, dimethyl acetamide, butyl acetate, ethyl acetate, methoxyethyl acetate, and the like. The average particle diameter of the metal phthalocyanine nanocrystals is from about 0.5 to about 200 nm. In other embodiments, the average particle diameter can be from about 0.5 to about 20 nm.

The photogenerating layer can be of a thickness as illustrated herein and for example, from about 0.05 micron to about 10 microns, and more specifically, from about 0.25 micron to about 4 microns when, for example, the photogenerating compositions are present in an amount of from about 30 to about 75 percent by volume. The maximum thickness of this layer in embodiments is dependent primarily upon factors, such as photosensitivity, electrical properties and mechanical considerations. In embodiments, the pigment comprises 100% phthalocyanine nanocrystal. In other embodiments, the phthalocyanine nanocrystal may be present in the pigment in an amount of from about 10% to about 100%, or from about 60% to about 100% by weight of the total weight of the pigment]. In embodiments where the nanocrystal comprises less than 100% of the pigment, it will be mixed with other photogenerators, such as metal phthalocyanines, metal free phthalocyanines, alkylhydroxyl gallium phthalocyanines, hydroxygallium phthalocyanines, chlorogallium phthalocyanines, perylenes, bis(benzimidazo) perylene, titanyl phthalocyanines, and the like, and more specifically, vanadyl phthalocyanines, Type V hydroxygallium phthalocyanines, and inorganic components such as selenium, selenium alloys, and trigonal selenium]. The organic photosensitive pigment made from the above process may be used for a wide range of electrophotography applications. For example, as seen in FIG. 1, the organic photosensitive pigment made from the above process may be used in a CGL to effectuate efficient charge generation. In an embodiment, an imaging member 5 comprises a substrate 2, a charge generating layer 6 disposed on the substrate 2, at least one charge transport layer 7 disposed on the charge generating layer 6, and an anticurl back coating 1 disposed on the substrate 2 on a side opposite to the charge transport layer 7, wherein the charge generating layer 6 comprising an organic photosensitive pigment having a nanocrystal form made from the above-described process.

The process is easily adaptable to form different metal phthalocyanines. For example, the present embodiments may include any of the following metal phthalocyanines: copper phthalocyanine, silicon phthalocyanine, scandium phthalocyanine, titanium phthalocyanine, vanadium phthalocyanine, iron phthalocyanine, cobalt phthalocyanine, nickel phthalocyanine, zinc phthalocyanine, gallium phthalocyanine, germanium phthalocyanine, yttrium phthalocyanine, zirconium phthalocyanine, silver phthalocyanine, indium phthalocyanine, tin phthalocyanine, and mixtures and derivatives thereof. Any of these can be used to prepare organic photosensitive pigments for use in electrophotography applications.

In a particular embodiment, the organic photosensitive pigment is derived from a metal phthalocyanine nanocrystal that is copper phthalocyanine (CuPc). To prepare the copper phthalocyanine, as disclosed in the previously referenced article, the synthesis is performed with 15 ml aqueous solution containing 0.1 g copper (II) chloride, 1.6 g Sodium linoleate, 10 ml ethanol and 2 ml linoleic acid were added into a 40 ml autoclave or tube under agitation to form a ternary system of liquid (organic phase of o-dicyanobenzene, n-pentanol, ethanol and linoleic acid), solid (metal linoleate) and solution (aqueous phase of metal salts), then the system were sealed and treated in a temperature range of from about 140° C. to about 200° C. Under such temperature conditions, the o-dicyanobenzene polymerizes into Pcs, which then complexes with the metal ions from the metal linoleate solid phase to form various metal Pcs. When the nanocrystals reach certain sizes, the nanocrystals will separate from the bulky solution phase and can be collected in the form of solid powders. The nanoparticles can easily be dispersed in nonpolar solvents allowing for ease of coating.

Figure 3:
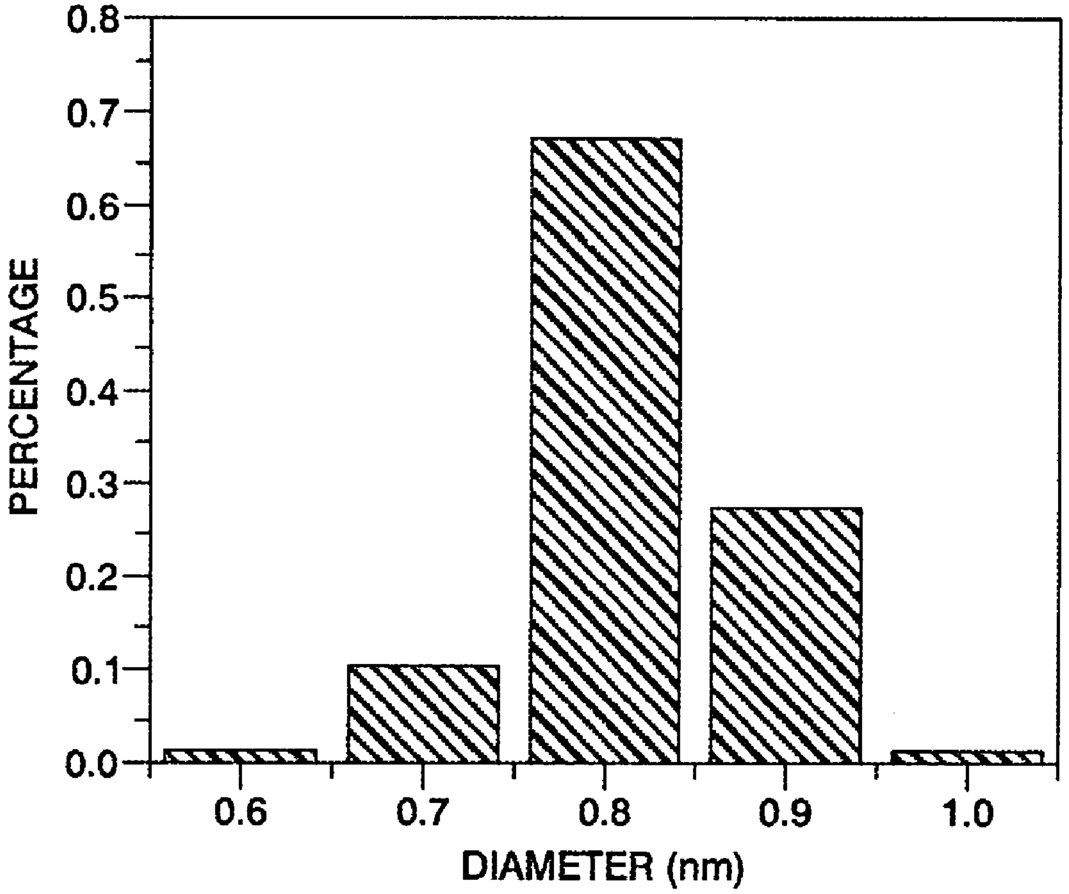
FIG. 3 is a histogram depicting particle diameters for copper phthalocyanine nanocrystals obtained from the present embodiments.

FIG. 2A is the chemical structure of copper phthalocyanine (Cu—Pcs), and FIG. 2B is a TEM image of Cu—Pcs nanoparticles having a particle diameter of about 0.6 nm. The image was obtained through measurement of the diameters of 200 particles. FIG. 3 is a histogram showing the diameter size distribution of 0.8±0.1 nm of the resulting Cu—Pcs nanoparticles.

The phase transfer process and the control of reactions at the different interfaces facilitate the monodispersity and variability of the nanocrystals obtained. The nanocrystals may be customized by modifying the reaction at the interfaces of the different phases. The resulting nanocrystals are generally round in shape with smooth surfaces. The diameters of the nanocrystals can be reasonably modified from about 4 to about 15 nm by changing temperature, the mole ratio of the protecting reagents to metal ions or the chain length of the fatty acid. By further changing these parameters, particles<4 nm may also be modified. It has been observed that concentrations and temperature are the main influential factors in a LSS system. To obtain substantially monodisperse nanocrystals, optimal concentration conditions of the corresponding metal ions are generally in the range of from about 0.03 to about 0.12 $mol/l^-$. Concentrations that are lower than 0.3 $mol/l^-$ suffer from low efficiency in production and concentrations that are higher than 0.12 $mol/l^-$ may lead to polydisperse nanocrystals. Different metal salts may also be used to obtain various metal Pcs with different properties.

While the description above refers to particular embodiments, it will be understood that many modifications may be made without departing from the spirit thereof. The accompanying claims are intended to cover such modifications as would fall within the true scope and spirit of embodiments herein.

The presently disclosed embodiments are, therefore, to be considered in all respects as illustrative and not restrictive, the scope of embodiments being indicated by the appended claims rather than the foregoing description. All changes that come within the meaning of and range of equivalency of the claims are intended to be embraced therein.

All the patents and applications referred to herein are hereby specifically, and totally incorporated herein by reference in their entirety in the instant specification.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

What is claimed is:

1. A process for preparing an organic photosensitive pigment having a nanocrystal form, comprising:

(a) combining together a liquid phase, a solid phase, and a solution to form a liquid-solid-solution, wherein the liquid phase comprises a fatty acid and an alcohol solvent, the solid phase comprises a sodium salt of the fatty acid, and the solution comprises metal salts;

(b) mixing the liquid-solid-solution to induce a phase transfer reaction;

(c) heating the reaction to generate phthalocyanine complexes with metal ions from the solid phase to form nanocrystals of the metal phthalocyanine, wherein the metal phthalocyanine nanocrystals have an average particle diameter of from about 0.5 to about 200 nm;

(d) preparing the metal phthalocyanine nanocrystals for use as an organic photosensitive pigment, wherein the metal phthalocyanine nanocrystals are present in the organic photosensitive pigment in an amount of from about 10% to about 100% by weight of a total weight of the organic photosensitive pigment.

2. The process of claim 1, wherein the metal phthalocyanine nanocrystals are further converted to a second nanocrystal form for use as the organic photosensitive pigment, the conversion comprising:

(e) mixing the metal phthalocyanine nanocrystals in a second solvent;

(f) filtering the converted plithalocyanine nanocrystals in a vacuum funnel;

(g) washing the converted phthalocyanine nanocrystals; and (h) drying the converted phthalocyanine nanocrystals in a vacuum oven.

3. The process of claim 1, wherein the metal phthalocyanine nanocrystal is copper phthalocyanine.

4. The process of claim 1, wherein the metal phthalocyanine nanocrystal is selected from the group consisting of copper phthalocyanine, silicon phthalocyanine, scandium phthalocyanine, titanium phthalocyanine, vanadium phthalocyanine, iron phthalocyanine, cobalt phthalocyanine, nickel phthalocyanine, zinc phthalocyanine, gallium phthalocyanine, germanium phthalocyanine, yttrium phthalocyanine, zirconium phthalocyanine, silver phthalocyanine, indium phthalocyanine, tin phthalocyanine, and mixtures thereof.

5. The process of claim 1, wherein the fatty acid is selected from the group consisting of butyric acid, caprioic acid, caprylic acid, capric acid, laurie acid, myristic acid, palmitic acid, stearic acid, arachidic acid, behenic acid, myristoleic acid, palmitoleic acid, oleic acid, linoleic acid, alpha-linoleinic acid, arachidonic acid, eicosapentaenoic acid, erucic acid, and docosahexaenoic acid, and mixtures thereof.

6. The process of claim 1, wherein the alcohol solvent has a formula $C_nH_{2n+2}O_x$, wherein n varies from 1 to 30 and x varies from 1 to 2, the formula including branched structures.

7. The process of claim 1, wherein the liquid phase further includes a reactive species selected from the group consisting of 1,2-dicyanobenzene and diiminoisoindoline, and mixtures thereof.

8. The process of claim 1, wherein the metal salt is selected from the group consisting of acetates, halides, bromates, chlorates, perchlorates, nitrates, nitrites, sulfonates, sulfites, phosphates, carbonates, benzoates, and mixtures thereof.

9. The process of claim 1, wherein the heating is performed at a temperature of from about 90° C. to about 200° C.

10. The process of claim 9, wherein the heating is performed at a temperature of from about 140° C. to about 200° C.

11. The process of claim 1, wherein the metal phthalocyanine nanocrystals have an average particle diameter of from about 0.5 to about 20 nm.

12. An organic photosensitive pigment having a nanocrystal form made from the process of claim 1.

13. An imaging member comprising:

a substrate;

a charge generating layer disposed on the substrate;

at least one charge transport layer disposed on the charge generating layer; and an anticurl back coating disposed on the substrate on a side opposite to the charge transport layer, the charge generating layer comprising an organic photosensitive pigment having a nanocrystal form made from the process of claim 1.

14. A process for preparing an organic photosensitive pigment having a nanocrystal form, comprising:

(a) combining together a liquid phase, a solid phase, and a solution to form a liquid-solid-solution, wherein the liquid phase comprises a fatty acid and an alcohol solvent, the solid phase comprises a sodium salt of the fatty acid, and the solution comprises metal salts;

(b) mixing the liquid-solid-solution to induce a phase transfer reaction between the solid phase and the solution phase, the reaction forming metal salts of the fatty acid in the solid phase;

(c) heating the reaction to generate phthalocyanine complexes with metal ions from the solid phase to form nanocrystals of the metal phthalocyanine, wherein the metal phthalocyanine nanocrystals have an average particle diameter of from about 0.5 to about 200 nm;

(d) collecting the metal phthalocyanine nanocrystals that separate out from the solution phase; and (e) preparing the metal phthalocyanine nanocrystals for use as an organic photosensitive pigment, wherein the metal phthalocyanine nanocrystals are present in the organic photosensitive pigment in an amount of from about 10% to about 100% by weight of a total weight of the organic photosensitive pigment.

15. The process of claim 14, wherein the metal phthalocyanine nanocrystals are further converted to a second nanocrystal form for use as the organic photosensitive pigment, the conversion comprising:

(f) mixing the metal phthalocyanine nanocrystals in a second solvent;

(g) filtering the converted phthalocyanine nanocrystals in a vacuum funnel;

(h) washing the converted phthalocyanine nanocrystals; and (i) drying the converted phthalocyanine nanocrystals in a vacuum oven.

16. The process of claim 14, wherein the fatty acid is linoleic acid, the alcohol solvent is ethanol, the sodium salt of the fatty acid is sodium linoleate, and the metal salts are acetate or chloride.

17. The process of claim 14, wherein the liquid phase further includes a reactive species selected from the group consisting of 1,2-dicyanobenzene and diiminoisoindoline, and mixtures thereof.

18. The process of claim 14, wherein the heating is performed at a temperature of from about 140° C. to about 200° C.

19. The process of claim 14, wherein the metal phthalocyanine nanocrystal is present in the organic photosensitive pigment in an amount of from about 60% to about 100% by weight of a total weight of the organic photosensitive pigment.

20. The process of claim 14, wherein the metal phthalocyanine nanocrystals have an average particle diameter of from about 0.5 to about 20 nm.

* * * * *